(12) United States Patent
Okamoto et al.

(10) Patent No.: US 9,365,472 B2
(45) Date of Patent: Jun. 14, 2016

(54) METHOD FOR PRODUCING CIS-1,3,3,3-TETRAFLUOROPROPENE

(71) Applicant: CENTRAL GLASS COMPANY, LIMITED, Ube, Yamaguchi (JP)

(72) Inventors: Satoru Okamoto, Kawagoe (JP); Naoto Takada, Kawagoe (JP); Fuyuhiko Sakyu, Kawagoe (JP); Takamasa Kitamoto, Kawagoe (JP); Takuya Tonomura, Kawagoe (JP); Masatomi Kanai, Kawagoe (JP)

(73) Assignee: CENTRAL GLASS COMPANY, LTD., Ube (JP)

( * ) Notice: Subject to any disclaimer, the term of this patent is extended or adjusted under 35 U.S.C. 154(b) by 0 days.

(21) Appl. No.: 14/583,349

(22) Filed: Dec. 26, 2014

(65) Prior Publication Data

US 2015/0112103 A1    Apr. 23, 2015

Related U.S. Application Data

(63) Continuation of application No. PCT/JP2013/067551, filed on Jun. 26, 2013.

(30) Foreign Application Priority Data

Jun. 29, 2012  (JP) ................................ 2012-147516
Jun. 25, 2013  (JP) ................................ 2013-132972

(51) Int. Cl.
*C07C 17/358*  (2006.01)
*B01J 27/125*  (2006.01)
(Continued)

(52) U.S. Cl.
CPC ............. *C07C 17/358* (2013.01); *B01J 27/125* (2013.01); *B01J 27/12* (2013.01); *B01J 27/132* (2013.01); *B01J 27/135* (2013.01); *C09K 3/30* (2013.01); *C09K 5/045* (2013.01)

(58) Field of Classification Search
CPC ..................................................... C07C 17/358
See application file for complete search history.

(56) References Cited

U.S. PATENT DOCUMENTS 2,480,560 A    8/1949  Downing et al.
6,124,510 A    9/2000  Elsheikh et al.
(Continued)

FOREIGN PATENT DOCUMENTS

JP    09-067281 A    3/1997
JP    11-140002 A    5/1999
(Continued)

OTHER PUBLICATIONS

"The Addition of Free Radicals to Unsaturated Systems. Part II. Radical Addition to Olefins of the Type R-CH:CH2." R. N. Haszeldine, et al., J. Chem. Soc. 1953, 1199-1206; CA 48 5787f.
(Continued)

*Primary Examiner* — Jafar Parsa
*Assistant Examiner* — Medhanit Bahta
(74) *Attorney, Agent, or Firm* — Typha IP LLC

(57) ABSTRACT

A method for producing 1234Z from 1234E while generation of 245fa as a byproduct is suppressed. The method for producing cis-1,3,3,3-tetrafluoropropene includes putting trans-1,3,3,3-tetrafluoropropene into contact with a catalyst. The trans-1,3,3,3-tetrafluoropropene is put into contact with the catalyst at a reaction temperature of higher than or equal to 200° C. and lower than or equal to 550° C. for a contact time of longer than or equal to 0.01 seconds and shorter than or equal to 500 seconds.

11 Claims, 1 Drawing Sheet

(51) Int. Cl.
*C09K 3/30* (2006.01)
*C09K 5/04* (2006.01)
*B01J 27/12* (2006.01)
*B01J 27/132* (2006.01)
*B01J 27/135* (2006.01)

(56) References Cited

U.S. PATENT DOCUMENTS

| 7,420,094 | B2* | 9/2008 | Petrov | C07C 17/358 |
| | | | | 570/123 |
| 7,485,760 | B2* | 2/2009 | Wang | C01B 7/191 |
| | | | | 570/156 |
| 2008/0058562 | A1 | 3/2008 | Petrov et al. | |
| 2008/0103342 | A1 | 5/2008 | Wang et al. | |
| 2009/0099395 | A1 | 4/2009 | Sakyu et al. | |
| 2010/0163781 | A1 | 7/2010 | Sharratt et al. | |
| 2010/0256426 | A1 | 10/2010 | Sakyu et al. | |
| 2012/0056122 | A1* | 3/2012 | Hulse | C01B 7/191 |
| | | | | 252/67 |

FOREIGN PATENT DOCUMENTS

| JP | 2000-063300 A | 2/2000 |
| JP | 2008-019243 A | 1/2008 |
| JP | 2008-110979 A | 5/2008 |
| JP | 2009-091301 A | 4/2009 |
| JP | 2009-108049 A | 5/2009 |
| JP | 2010-523635 A | 7/2010 |
| WO | 2008/030443 A1 | 3/2008 |

OTHER PUBLICATIONS

"Reactions of Fluoro Olefins, Communication 13, Catalytic Hydrogenation of Perfluoro Olefins", I. L. Knunyants et al., Izvestiya Akademil Nauk SSSR, Otdelenie Khimicheskikh Nauk, No. 8, pp. 1412-1418, Aug. 1960.
International Search Report of PCT/JP2013/067551 mailed on Sep. 17, 2013, corresponding to the present application.
International preliminary Report on Patentability of PCT/JP2013/067551 mailed on Dec. 31, 2014, corresponding to the present application.
Written Opinion of the International Searching Authority of PCT/JP2013/067551 mailed on Sep. 17, 2013, corresponding to the present application.

\* cited by examiner

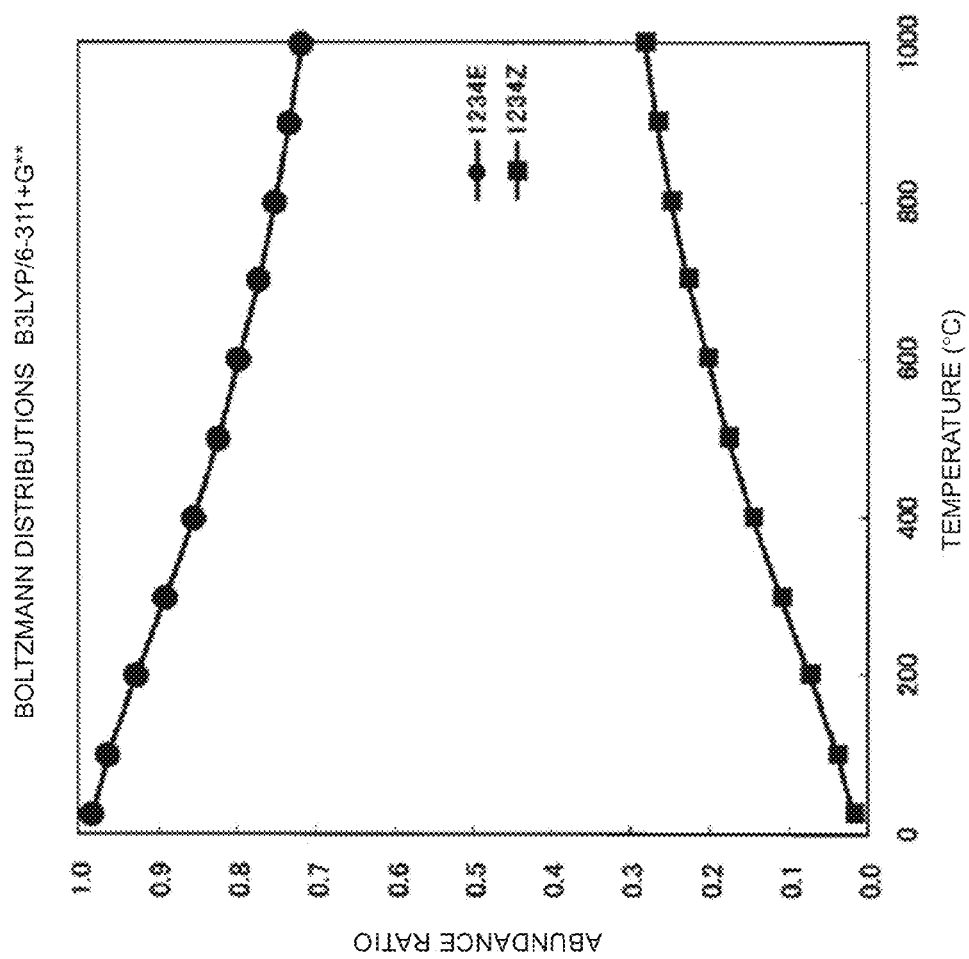

METHOD FOR PRODUCING CIS-1,3,3,3-TETRAFLUOROPROPENE

CROSS REFERENCE TO RELATED APPLICATION

This application is based upon and claims the benefit of priority from Japanese Patent Applications No. 2012-147516 filed on Jun. 29, 2012 and No. 2013-132972 filed on Jun. 25, 2013 and the prior PCT Application PCT/JP2013/067551 filed on Jun. 26, 2013, the entire contents of which are incorporated herein by reference.

FIELD

The present invention relates to a method for producing cis-1,3,3,3-tetrafluoropropene useful for a foaming agent, a solvent, a flux, a washing detergent, a working fluid, an agro-medical intermediate and a semiconductor-related material that do not much influence the global environment, and more specifically to a method for producing cis-1,3,3,3-tetrafluoropropene by isomerization performed on trans-1,3,3,3-tetrafluoropropene.

BACKGROUND 1,3,3,3-tetrafluoropropene has isomers, namely, a cis isomer and a trans isomer. Hereinafter, a cis isomer may be referred to as "1234Z", and a trans isomer may be referred to as "1234E". A mixture of a cis isomer and a trans isomer may be referred to as "1234" or "1234EZ". In the case where it is not intended to distinguish whether the isomer is a cis isomer or a trans isomer, the isomer will be also referred to as "1234" or "1234EZ".

1234Z has a double bond in a molecule and therefore has a very short atmospheric life time, and thus has substantially no influence on global warming or depletion of ozone layer. 1234Z has a boiling point of 9° C. and thus is useful as an intermediate for a functional substance such as a washing detergent, a flux, a coolant, a spray, a working fluid or the like and for any of various functional products.

Conventionally known methods for producing 1,3,3,3-tetrafluoropropene include a method of dehydroiodinating 1,3,3,3-tetrafluoro-1-iodopropane by use of alcoholic potassium hydroxide (R. N. Haszeldine, et al., J. Chem. Soc. 1953, 1199-1206; CA 48 5787f) and a method of dehydrofluorinating 1,1,1,3-3-pentafluoropropane (245fa) by use of potassium hydroxide in dibutylether (I. L. Knunyants, et al., Izvest. Akad. Nauk. S. S. S. R., Otdel. Khim. Nauk. 1960, 1412-18; CA 55, 349f).

Japanese Laid-Open Patent Publication No. H11-140002 discloses a method of dehydrofluorinating 1,1,1,3,3-pentafluoropropane by use of a chromium/activated carbon catalyst to produce 1,3,3,3-tetrafluoropropene, and Japanese Laid-Open Patent Publication No. 2000-63300 discloses a method of putting 1,1,1,3,3-pentafluoropropane into contact with a chromium-based catalyst to produce 1,3,3,3-tetrafluoropropene.

Meanwhile, there are methods for producing propene by use of a dehydrofluorination reaction performed on a general fluoroalkane compound in a gas phase. For example, Japanese Laid-Open Patent Publication No. H9-67281 discloses a method of putting 1,1,1,3,3,3-hexafluoropropane in a gas state into contact with an activated carbon catalyst or a chromium oxide catalyst to produce corresponding propene. U.S. Pat. No. 2,480,560 discloses a method of putting fluoroethane into contact with activated carbon to cause thermal decomposition and thus to produce propene.

Japanese Laid-Open Patent Publication No. 2008-019243 discloses a method for produce 1,3,3,3-tetrafluoropropene by dehydrofluorinating 1,1,1,3,3-pentafluoropropane in a gas phase with use of a zirconium compound-supported catalyst in which a zirconium compound is supported on a metal oxide or activated carbon.

By these methods, however, 1234 is usually obtained as a mixture of a cis isomer (1234Z) and a trans isomer (1234E). This is inconvenient when only one of the isomers is to be used.

In such a background, it has been attempted to cause mutual conversion by isomerization of fluoroalkene. Japanese PCT National Phase Laid-Open Patent Publication No. 2010-523635 discloses a method by which E-(hydrohalo)fluoroalkene, which is a trans isomer, is put into contact with a solid catalyst such as a Lewis acid catalyst, a chromia-containing catalyst, an alumina catalyst or the like and is isomerized into Z-(hydrohalo)fluoroalkene, which is a cis isomer, by a gas phase reaction by utilization of an equilibrium reaction.

International Publication No. WO2008/030443 discloses a method by which trans-1,3,3,3-tetrafluoropropene is isomerized into cis-1,3,3,3-tetrafluoropropene by use of a chromium oxide catalyst.

SUMMARY

It is described in examples 1 to 3 of International Publication No. WO2008/030443 that a composition obtained by use of chromium oxide as a catalyst contains about 3.8 to 5% by mass of 1,1,1,3,3-pentafluoropropane (245fa). A reason for this is that the target compound, 1234Z, can be obtained by isomerization of 1234E, but fluorination is also advanced and a high-order fluorination product, namely, 1,1,1,3,3-pentafluoropropane (245fa) is easily produced as a byproduct.

In an isomerization reaction of 1234E into 1234Z, 1234Z as the target compound and 245fa form azeotropy or an azeotrope-like composition. Therefore, 1234Z and 245fa cannot be substantially separated from each other by distillation. Namely, once 245fa is produced as a byproduct during the isomerization reaction of 1234E into 1234Z, it is difficult to obtain highly pure 1234Z by the currently available technology.

The present invention made in light of the above-described problems has an object of producing 1234Z efficiently by an isomerization reaction of 1234E while 1,1,1,3,3-pentafluoropropane is suppressed from being produced as a byproduct.

Namely, the present invention is as follows.

[Invention 1]

A method for producing cis-1,3,3,3-tetrafluoropropene comprises contacting trans-1,3,3,3-tetrafluoropropene with a catalyst at a reaction temperature of higher than or equal to 200° C. and lower than or equal to 550° C. for a contact time of longer than or equal to 0.01 seconds and shorter than or equal to 500 seconds.

[Invention 2]

A method according to invention 1, the reaction temperature may be higher than or equal to 250° C. and lower than or equal to 500° C. and the contact time may be longer than or equal to 1 second and shorter than or equal to 150 seconds.

[Invention 3]

A method according to invention 1 or 2, the reaction temperature and the contact time may have negative correlation.

[Invention 4]

A method according to any one of inventions 1 to 3, wherein contacting the trans-1,3,3,3-tetrafluoropropene with the catalyst may comprise contacting the trans-1,3,3,3-tetrafluoropropene with a gas phase.

[Invention 5]

A method according any one of inventions 1 to 4, the catalyst may be a metal compound comprising at least one metal material selected from the group consisting of aluminum, chromium, titanium, manganese, iron, nickel, cobalt, copper, magnesium, zirconium, molybdenum, zinc, tin, lanthanum and antimony.

[Invention 6]

A method according to invention 5, the metal compound may be a metal fluoride.

[Invention 7]

A method for producing highly pure cis-1,3,3,3-tetrafluoropropene may comprise distilling cis-1,3,3,3-tetrafluoropropene obtained by a method according to any one of inventions 1 to 6.

[Invention 8]

A method according to any one of inventions 1 to 7, the produced cis-1,3,3,3-tetrafluoropropene may be substantially free of 1,1,1,3,3-pentafluoropropane.

[Invention 9]

A method for producing cis-1,3,3,3-tetrafluoropropene includes putting trans-1,3,3,3-tetrafluoropropene into contact with a catalyst at a reaction temperature of higher than or equal to 200° C. and lower than or equal to 550° C. for a contact time of longer than or equal to 0.01 seconds and shorter than or equal to 500 seconds, wherein the catalyst may be supported catalyst in which a metal compound comprising at least one metal material selected from the group consisting of aluminum, chromium, titanium, manganese, iron, nickel, cobalt, copper, magnesium, zirconium, molybdenum, zinc, tin, lanthanum and antimony is supported on carbon.

According to the present invention, 1234Z is produced by an isomerization reaction of 1234E efficiently while 1,1,1,3,3-pentafluoropropane is suppressed from being produced as a byproduct. Therefore, the resultant 1234Z does not substantially contain 1,1,1,3,3-pentafluoropropane, which is difficult to be separated from 1234Z by distillation. Thus, 1234Z can be purified easily by distillation, and highly pure 1234Z can be produced.

BRIEF DESCRIPTION OF DRAWINGS

FIG. 1 shows calculation results on Boltzmann distributions of 1234Z and 1234E.

DESCRIPTION OF EMBODIMENTS

According to a method for producing cis-1,3,3,3-tetrafluoropropene (1234Z) of the present invention, trans-1,3,3,3-tetrafluoropropene (1234E) is put into contact with an isomerization catalyst and is converted into cis-1,3,3,3-tetrafluoropropene (1234Z).

The present invention has a feature that isomerization conditions such as the reaction temperature, the contact time and the type (material) of the catalyst and the like are appropriately selected, so that the effect of decreasing the amount of 1,1,1,3,3-pentafluoropropane (245fa) produced as a byproduct to a very low level in the isomerization reaction of 1234E into 1234Z is provided.

1234Z obtained by the present invention does not substantially contain 1,1,1,3,3-pentafluoropropane (245fa). Herein, the expression "not substantially contain" refers to that, for example, the content of 1,1,1,3,3-pentafluoropropane (245fa) in a composition that is obtained by the isomerization reaction and contains 1234Z as a main component is lower than or equal to 1% by mass. 1234Z is often required to have a purity of higher than or equal to 99% by mass when being used for a common chemical product such as a foaming agent, a solvent or the like. In the field of electronic materials and coolants, 1234Z may be even required to have a purity of 99.9 to 99.99% by mass. As can be seen from this, raising the purity of 1234Z is an important issue.

The reaction system may be a gas phase reaction system or a liquid phase reaction system. The processing system may be a flow system or a batch system. Any combination of such a reaction system and such a processing system is appropriately usable. Practically, a gas phase flow system is most preferable because the chemical substances involved in the reaction have a low boiling point. In the gas phase flow system, the catalyst may be held by a fixed bed, a fluidized bed, a moving bed or the like. Use of a fixed bed is simple and preferable.

In the following description, a gas phase reaction will be described. In the case where a liquid phase reaction is used, a person of ordinary skill in the art would modify the following method when necessary based on the technological common knowledge so that the conditions are optimized.

[Material]

Trans-1,3,3,3-tetrafluoropropene (1234E), which is used as a material according to the present invention, can be produced by a known method. For example, trans-1,3,3,3-tetrafluoropropene is known to be easily synthesizable by a reaction of 1,1,1,3,3-pentafluoropropane (245fa), which is industrially available, and a base such as sodium hydroxide or the like. 1234E purified by deoxidation, drying, distillation and the like is preferable as the material. 1234E is also available as a product because it is industrially produced as fireproof cover gas used for producing a magnesium alloy.

Needless to say, a mixture of 1234E and 1234Z is usable. It should be noted that the ratio of 1234Z/1234E is preferably 0 to 0.2. It is more preferable that the ratio of 1234Z/1234E is closer to zero. A reason for this is that the ratio of 1234Z/1234E of the reaction product is dominated by thermodynamic equilibrium. In the case where a material in a state of thermodynamic equilibrium is used, the composition of the generated gas is theoretically the same as that of the material gas. 1234E and 1234Z are easily separable by distillation. Therefore, in the case where a mixture of 1234E and 1234Z is used as the material, it is preferable to distill the mixture in advance to separate 1234E and 1234Z from each other. It is reasonable that purified gas obtained by the isomerization reaction is collected, 1234Z as the target compound is isolated by distillation or the like, and unreacted 1234E is used again for the present invention as a material. Inert gas such as nitrogen or the like may be supplied together with the material, but it should be noted that supply of an excessive amount of inert gas may decrease the productivity.

The method according to the present invention is performed as follows. A reactor formed of a material substantially inactive to hydrogen fluoride is used. 1234E is introduced into a reaction area filled with a catalyst having the temperature thereof adjusted. The reactor is usually tubular, and is formed of stainless steel, Hastelloy™, Monel™, platinum, carbon, a fluorine resin or a material lined with such a substance.

[Catalyst]

According to the present invention, any catalyst that converts 1234E into 1234Z by contacting 1234E is usable. Such a catalyst may be a metal compound containing a metal material. The catalyst may be a non-supported catalyst or a supported catalyst.

As a non-supported catalyst, a metal fluoride containing a metal material is preferable. The metal material contained in the catalyst is at least one metal material selected from the group consisting of aluminum, chromium, manganese, zirconium, titanium and magnesium. These metal materials may be used independently or as a composite metal containing two or more metal materials. A metal fluoride containing such a metal material is obtained by fluorinating a metal oxide that is obtained by oxidizing such a metal material. In this specification, the term "metal fluoride" refers to a metal oxide having a part of, or the entirety of, the oxygen atoms thereof substituted with fluorine atoms. A metal oxide which is usable as a material of a metal fluoride is available in a plurality of crystal systems. A metal oxide of any crystal system is usable. As alumina, γ-alumina has a large surface area and thus is preferable.

A preferable composite metal contains, as a main component, aluminum, chromium, manganese, zirconium, titanium or magnesium, and contains, as a sub component, aluminum, chromium, titanium, manganese, iron, nickel, copper, cobalt, magnesium, zirconium, molybdenum, antimony or the like. Examples of preferable composite metals include a composite metal of alumina and chromium, a composite metal of alumina and zirconia, a composite metal of alumina and titania, and a composite metal of alumina and magnesia. An oxide of any of such composite metals contains aluminum preferably at a content of higher than or equal to 50% by atom, and more preferably at a content of higher than or equal to 80% by atom. When the content of aluminum is lower than 50% by atom, the conversion rate of isomerization is low and thus an oxide having such an aluminum content is not preferable.

A metal oxide which is usable as a material of a metal fluoride may assume one or more crystal forms. For example, alumina is available as γ-alumina and α-alumina, and titania is available as anatase and rutile. A metal oxide of any crystal form is usable. In the case of alumina, γ-alumina has a large surface area and is preferable.

For the isomerization reaction according to the present invention, a metal fluoride is used as a catalyst. In the case where a non-fluorinated metal oxide is used, hydrogen fluoride and 1,3,3,3-tetrafluoropropene each act as a fluorination agent. Therefore, the metal oxide is converted into a metal fluoride along with time, and thus the reaction tends to be unstable. For this reason, a preferable catalyst is a metal fluoride obtained by fluorinating a metal oxide in advance. For such a metal fluoride generated by fluorinating a metal oxide, the ratio of the oxygen atoms substituted with fluorine atoms is not limited to any specific ratio and may be any ratio in a wide range. Any ratio in a wide range is usable. A metal fluoride having all the oxygen atoms thereof substituted with fluorine atoms, or a metal fluoride having a part of the oxygen atoms thereof substituted with fluorine atoms, may be used.

A metal fluoride is prepared by putting a fluorination agent such as hydrogen fluoride, fluorinated hydrocarbon, fluorinated-chlorinated hydrocarbon or the like into contact with a metal oxide or an oxide of a composite metal described above. It is usually preferable that the fluorination is performed step by step. In the case where the fluorination is performed by use of hydrogen fluoride, a large amount of heat is generated. Therefore, it is preferable that the metal oxide is first fluorinated at relatively low temperature by use of diluted hydrofluoric acid or hydrogen fluoride gas, and then the concentration and/or the temperature is gradually raised. The final stage of fluorination is preferably performed at a temperature higher than or equal to the isomerization reaction temperature. In order to prevent time-wise change during the reaction, it is preferable that the fluorination is performed by use of hydrogen fluoride at a temperature of higher than or equal to 200° C., higher than or equal to 400° C., or even higher than or equal to 500° C. There is no upper limit on the temperature. When the temperature exceeds 900° C., the fluorination is difficult because of the level of heat resistance of the fluorination device. Practically, it is preferable to perform the fluorination at a temperature of lower than or equal to 600° C. As described above, in order to prevent a change in the composition of catalyst during the reaction, it is preferable to use, as a catalyst, a metal fluoride obtained by fluorinating a metal oxide by use of a fluorination agent such as hydrogen fluoride, fluorinated hydrocarbon, fluorinated-chlorinated hydrocarbon or the like at a predetermined temperature higher than or equal to the reaction temperature.

According to the present invention, a supported catalyst in which a metal compound is supported may be used. As a support of the supported catalyst used in the present invention, carbon or a metal material described above as a non-supported catalyst (including a composite metal containing two or more metal materials) is usable. The metal that is used as the support may be a metal oxide. For example, a metal oxide containing at least one metal material selected from the group consisting of aluminum, chromium, manganese, zirconium, titanium and magnesium may be used as the support independently. Alternatively, a composite metal oxide containing two or more metal materials described above may be used as the support. A preferable composite metal oxide, for example, contains, as a main component, an oxide of aluminum, chromium, manganese, zirconium, titanium, or manganese, and contains, as a sub component, an oxide of aluminum, chromium, titanium, manganese, iron, nickel, copper, cobalt, magnesium, zirconium, molybdenum, antimony or the like.

A metal material contained in the metal compound to be supported on the support is, for example, aluminum, chromium, titanium, manganese, iron, nickel, cobalt, copper, magnesium, zirconium, molybdenum, zinc, tin, lanthanum, antimony or the like. Among these, aluminum, chromium, titanium, iron, nickel, cobalt, copper, zirconium, zinc, tin, lanthanum, and antimony are preferable. These metal materials are each supported as a fluoride, a chloride, a fluoride-chloride, an oxyfluoride, an oxychloride, an oxyfluoridechloride or the like. Two or more metal compounds may be supported together.

Specific examples of the metal compound to be supported include chromium nitrate, chromium trichloride, potassium dichromate, titanium trichloride, manganese nitrate, manganese chloride, iron (III) chloride, nickel nitrate, nickel chloride, cobalt nitrate, cobalt chloride, antimony pentachloride, magnesium chloride, magnesium nitrate, zirconium chloride, zirconium oxychloride, zirconium nitrate, copper (II) chloride, zinc (II) chloride, lanthanum nitrate, tin tetrachloride, and the like.

In order to prevent a change in the composition of catalyst during the isomerization reaction, it is preferable that a catalyst, prepared by causing a metal compound described above to be supported on a support, is fluorinated, before being used, by a fluorination agent such as hydrogen fluoride, fluorinated hydrocarbon, fluorinated-chlorinated hydrocarbon or the like at a predetermined temperature higher than or equal to the reaction temperature by a method substantially the same as the above-described method for fluorinating the metal oxide.

In the case where the support is a metal oxide and a layer of a supported metal compound covers the entirety of the support, the support is not fluorinated and only the supported metal compound is fluorinated in the fluorination step. In the isomerization step, only the supported metal compound acts as the catalyst. By contrast, in the case where the support is a metal oxide and a layer of a supported metal compound does not cover the entirety of the support, both of the supported metal compound and the support are fluorinated in the fluorination step. In the isomerization step, the support may act as a catalyst together with the supported metal compound. In such a case where the support acts as a catalyst together with the supported metal compound, the metal compound and the support may act like a non-supported catalyst as a composite metal fluoride, not as a supported catalyst.

Specific preferable examples of the isomerization catalyst according to the present invention include fluorinated alumina, fluorinated chromia, and chromium-supported activated carbon. Fluorinated alumina and fluorinated chromia are especially preferable. Needless to say, it is preferable that these catalysts are fluorinated before the reaction.

The ratio by mass of the metal material with respect to the entirety of the catalyst including the support and the supported metal compound is 0.1 to 80% by mass, and preferably 1 to 50% by mass. When the ratio is lower than 0.1% by mass, the catalyst effect is low, which is not preferable. When the ratio exceeds 80% by mass, it is difficult to stably support the metal material on the support, which is not preferable. In the case where the supported metal compound is a solid metal salt, the ratio by mass of the metal material with respect to the entirety of the catalyst is 0.1 to 40% by mass, and preferably 1 to 30% by mass.

[Reaction Temperature]

As shown by the calculation example of Boltzmann distributions (see FIG. 1), as the temperature is higher, the 1234Z/1234E ratio is higher and the reaction rate is also higher, which is preferable. However, when the reaction temperature for the isomerization reaction of converting 1234E into 1234Z according to the present invention is higher than or equal to 600° C., 1234E and/or 1234Z may be decomposed or coked on the catalyst, which is not preferable. In addition, setting the reaction temperature to a level higher than necessary causes waste of energy and increases the load on the device. By contrast, when the reaction temperature is lower than 100° C., the reaction rate is too low for practical use. Therefore, the isomerization reaction temperature is preferably higher than or equal to 150° C. and lower than or equal to 600° C., and especially preferably higher than or equal to 200° C. and lower than or equal to 550° C. More preferably, the isomerization reaction temperature is higher than or equal to 250° C. and lower than or equal to 500° C. The reaction temperature and the contact time during which 1234E is in contact with the catalyst have negative correlation. It is preferable for the production efficiency of 1234Z that when the reaction temperature is high, the contact time is short, and that when the reaction temperature is low, the contact time is long.

[Contact Time]

Usually in the case of a gas phase flow system, the productivity is often discussed with a value (second) obtained by dividing the volume (ml) of the reaction zone by the material supply rate (ml/sec). In the case where the reaction zone is filled with a catalyst, such a value is referred to as "contact time". An optimal contact time according to the present invention is longer than or equal to 0.01 seconds and shorter than or equal to 500 seconds, preferably longer than or equal to 0.1 seconds and shorter than or equal to 250 seconds, and more preferably longer than or equal to 1 second and shorter than or equal to 150 seconds. In general, when the contact time is shorter than the above, the conversion ratio may be significantly different from the ratio providing the thermodynamic equilibrium composition. By contrast, when the contact time is longer than the above, the productivity may be poor or the material and/or the product may be turned into tar even if the conversion ratio is close to the ratio providing the equilibrium composition.

For the isomerization reaction according to the present invention, an appropriate combination of reaction time and contact time is an important element. When the reaction temperature is higher than or equal to 200° C. and lower than or equal to 550° C., it is preferable that the contact time is longer than or equal to 0.01 seconds and shorter than or equal to 500 seconds. When the reaction temperature is higher than or equal to 250° C. and lower than or equal to 500° C., it is preferable that the contact time is longer than or equal to 1 second and shorter than or equal to 150 seconds.

A product of the isomerization reaction is washed to remove an acid component, dried with zeolite or the like, and then subjected to a common distillation operation so that 1234E and 1234Z can be separated from each other. Especially when 1234E that does not contain impurities other than 1234Z is used as the material, highly pure 1234Z can be produced easily.

[Other Parameters, Pressure]

There is no specific limitation on the reaction pressure. It is easy to perform the operation at normal pressure or in the vicinity thereof. It should be noted that a reaction pressure higher than or equal to 1 MPa requires a costly high-pressure-resistant device and also may cause undesirable polymerization of the material or the product. There is no specific limitation on the method for heating the device. It is preferable that the device is directly heated by an electric heater or a burner, or indirectly heated by use of melted salt or sand.

[1234zc]

As a result of the isomerization reaction according to the present invention, 1,1,3,3-tetrafluoropropene (1234zc) may be occasionally produced as a byproduct. 1234zc is separable from cis-1,3,3,3-tetrafluoropropene (1234Z) by distillation, but requires a distillation column having a large number of theoretical stages for the separation because the boiling point thereof is close to that of 1234Z. Therefore, it is preferable that the amount of generation of 1234zc is decreased during the isomerization reaction.

EXAMPLES

Hereinafter, the present invention will be specifically described by way of examples. The present invention is not limited to the following examples. Herein, "%" used for a composition analysis value represents the "surface area %" of a composition of a reaction mixture measured by use of gas chromatography (detector: FID). Each displayed value is obtained by rounding off the numeral at the place smaller by one digit than the smallest place of the displayed value. For example, 0.01% in the tables represents a value smaller than 0.015 surface area %.

Preparation Example 1

A cylindrical stainless steel (SUS316L) reaction tube having a diameter of 2 cm and a length of 40 cm and equipped with an electric furnace was filled with 50 ml of granular γ-alumina (Sumika Alchem Co., Ltd.; KHS-46). The temperature was raised to 200° C. while nitrogen gas was flowing. When water was recognized to stop flowing out, hydrogen fluoride (HF) was supplies together with nitrogen gas, and the concentration of hydrogen fluoride (HF) was gradually raised. When a hot spot generated by fluorination of alumina as the filler reached an exit end of the reaction tube, the temperature of the reactor was raised step by step in increments of 100° C. while being kept for 1 hour at each step. The substance in the reaction tube was kept at a final temperature of 500° C. for 1 hour to fluorinate the catalyst material, thus to prepare a catalyst.

Preparation Example 2

Preparation was performed in substantially the same manner as in preparation example 1 except that the reaction tube was filled with granular chromia (produced by JGC Catalysts and Chemicals Ltd.; E01W-1) instead of the granular γ-alumina.

Preparation Example 3

Preparation was performed in substantially the same manner as in preparation example 1 except that the reaction tube was filled with granular zirconia (produced by Saint-Gobain K.K.; SZ31163) instead of the granular γ-alumina.

Preparation Example 4

Preparation was performed in substantially the same manner as in preparation example 1 except that the reaction tube was filled with granular titania (produced by Saint-Gobain K.K.; ST61120) instead of the granular γ-alumina.

Preparation Example 5

Preparation was performed in substantially the same manner as in preparation example 1 except that the reaction tube was filled with granular manganese (IV) oxide (produced by Kanto Chemical Co., Inc.) instead of the granular γ-alumina.

Preparation Example 6

20% by mass of aqueous solution of chromium chloride was prepared in a triangular flask, and 110 ml of Shirosagi, granular activated carbon (produced by Takeda EnrivoChemicals, Ltd.; G2X), was put thereto and kept for 3 hours. Activated carbon was filtrated and dried at 70° C. at low pressure by use of a rotary evaporator. A cylindrical stainless steel (SUS316L) reaction tube having a diameter of 2 cm and a length of 40 cm and equipped with an electric furnace was filled with 50 ml of chromium chloride-supported activated carbon. The temperature was raised to 200° C. while nitrogen gas was flowing. When water was recognized to stop flowing out, hydrogen fluoride (HF) was supplied together with nitrogen gas, and the concentration of hydrogen fluoride (HF) was gradually raised. When a hot spot generated by fluorination of the filler reached an exit end of the reaction tube, the temperature of the reactor was raised step by step in increments of 100° C. while being kept for 1 hour at each step. The substance in the reaction tube was kept at a final temperature of 500° C. for 1 hour to fluorinate the supported catalyst, thus to prepare a catalyst.

Preparation Example 7

A catalyst was prepared in substantially the same manner as in preparation example 6 except that 29% by mass of aqueous solution of iron (III) chloride was used instead of 20% by mass of aqueous solution of chromium chloride.

Preparation Example 8

A catalyst was prepared in substantially the same manner as in preparation example 6 except that 18% by mass of aqueous solution of cobalt (II) chloride was used instead of 20% by mass of aqueous solution of chromium chloride.

Preparation Example 9

A catalyst was prepared in substantially the same manner as in preparation example 6 except that 17% by mass of aqueous solution of nickel (II) chloride was used instead of 20% by mass of aqueous solution of chromium chloride.

Preparation Example 10

A catalyst was prepared in substantially the same manner as in preparation example 6 except that 26% by mass of aqueous solution of copper (II) chloride was used instead of 20% by mass of aqueous solution of chromium chloride.

Preparation Example 11

A catalyst was prepared in substantially the same manner as in preparation example 6 except that 21% by mass of aqueous solution of zinc (II) chloride was used instead of 20% by mass of aqueous solution of chromium chloride.

Preparation Example 12

Shirosagi, granular activated carbon (produced by Takeda EnrivoChemicals, Ltd.; G2X), was dried at 150° C. at low pressure by use of a rotary evaporator. 46 g of tin tetrachloride (produced by Kanto Chemical Co., Inc.) was dripped onto 110 ml of the dried activated carbon (about 46 g) under slow stirring. A cylindrical stainless steel (SUS316L) reaction tube having a diameter of 2 cm and a length of 40 cm and equipped with an electric furnace was filled with 50 ml of tin tetrachloride-supported activated carbon. The temperature was raised to 80° C. while nitrogen gas was flowing. Then hydrogen fluoride (HF) was supplied together with nitrogen gas, and the concentration of hydrogen fluoride (HF) was gradually raised. After a hot spot generated by fluorination of the filler reached an exit end of the reaction tube, the substance in the reaction tube was kept in the state for 1 hour to prepare a catalyst.

Preparation Example 13

A catalyst was prepared in substantially the same manner as in preparation example 12 except that 46 g of antimony pentachloride (produced by Wako Pure Chemical Industries, Ltd.) was used instead of tin tetrachloride.

Preparation Example 14

A catalyst was prepared in substantially the same manner as in preparation example 6 except that 12% by mass of aqueous solution of lanthanum (III) nitrate was used instead of 20% by mass of aqueous solution of chromium chloride.

Examples 1 to 17 and Comparative Examples 1 to 5

A cylindrical stainless steel (SUS316L) reaction tube having a diameter of 2 cm and a length of 40 cm and equipped with an electric furnace was filled with 50 ml of the catalyst prepared in preparation example 1, and the temperature of the reaction tube was raised to 200° C. while nitrogen gas was flowing at a flow rate of about 100 ml/min.

Next, trans-1,3,3,3-tetrafluoropropene (99.9%) as a material, which had been gasified in advance, was started to be supplied to the reaction tube at a rate calculated based on the contact time. When the flow rate of the organic substance was stabilized, the supply of nitrogen gas was stopped.

An isomerization reaction was performed with a contact time in the range of 5 to 1000 seconds at a reaction temperature in the range of 147° C. to 500° C. Table 1 shows the results (examples 1 to 17 and comparative examples 1 to 5). Two hours after the start of the reaction, the reaction was stabilized. Thus, the gas flowing out of the reactor was blown into water to remove acid gas. The resultant product was analyzed by gas chromatography. The resultant product was subjected to precision distillation to obtain purified 1234Z. Table 1 shows the isomerization conditions including the reaction temperature and the contact time in examples 1 to 17 and comparative examples 1 to 5. The post-distillation purity of 1234Z shown in Table 1 is obtained by calculation as a purity of a mixture of 1234Z and 245fa because 245fa is not substantially separable even by distillation performed on 1234Z.

Examples 18 to 25

A reaction was performed in substantially the same manner as in [Examples 1 to 17 and comparative examples 1 to 5] except that the catalyst prepared in preparation example 2 was used and that the isomerization conditions were different. Table 2 shows the results and the isomerization conditions.

Examples 26 to 32

A reaction was performed in substantially the same manner as in [Examples 1 to 17 and comparative examples 1 to 5] except that the catalyst prepared in preparation example 3 was used and that the isomerization conditions were different. Table 3 shows the results and the isomerization conditions.

Examples 33 to 42

A reaction was performed in substantially the same manner as in [Examples 1 to 17 and comparative examples 1 to 5] except that the catalyst prepared in preparation example 4 was used and that the isomerization conditions were different. Table 4 shows the results and the isomerization conditions.

Examples 43 to 46

A reaction was performed in substantially the same manner as in [Examples 1 to 17 and comparative examples 1 to 5] except that the catalyst prepared in preparation example 5 was used and that the isomerization conditions were different. Table 5 shows the results and the isomerization conditions.

Examples 47 to 57

A reaction was performed in substantially the same manner as in [Examples 1 to 17 and comparative examples 1 to 5] except that the catalyst prepared in preparation example 6 was used and that the isomerization conditions were different. Table 6 shows the results and the isomerization conditions.

Examples 58 to 68

A reaction was performed in substantially the same manner as in [Examples 1 to 17 and comparative examples 1 to 5] except that the catalyst prepared in preparation example 7 was used and that the isomerization conditions were different. Table 7 shows the results and the isomerization conditions.

Examples 69 to 80

A reaction was performed in substantially the same manner as in [Examples 1 to 17 and comparative examples 1 to 5] except that the catalyst prepared in preparation example 8 was used and that the isomerization conditions were different. Table 8 shows the results and the isomerization conditions.

Examples 81 to 92

A reaction was performed in substantially the same manner as in [Examples 1 to 17 and comparative examples 1 to 5] except that the catalyst prepared in preparation example 9 was used and that the isomerization conditions were different. Table 9 shows the results and the isomerization conditions.

Examples 93 to 98

A reaction was performed in substantially the same manner as in [Examples 1 to 17 and comparative examples 1 to 5] except that the catalyst prepared in preparation example 10 was used and that the isomerization conditions were different. Table 10 shows the results and the isomerization conditions.

Examples 99 to 111

A reaction was performed in substantially the same manner as in [Examples 1 to 17 and comparative examples 1 to 5] except that the catalyst prepared in preparation example 11 was used and that the isomerization conditions were different. Table 11 shows the results and the isomerization conditions.

Examples 112 to 117

A reaction was performed in substantially the same manner as in [Examples 1 to 17 and comparative examples 1 to 5] except that the catalyst prepared in preparation example 12 was used and that the isomerization conditions were different. Table 12 shows the results and the isomerization conditions.

Examples 118 to 126

A reaction was performed in substantially the same manner as in [Examples 1 to 17 and comparative examples 1 to 5] except that the catalyst prepared in preparation example 13 was used and that the isomerization conditions were different. Table 13 shows the results and the isomerization conditions.

Examples 127 to 133

A reaction was performed in substantially the same manner as in [Examples 1 to 17 and comparative examples 1 to 5] except that the catalyst prepared in preparation example 14 was used and that the isomerization conditions were different. Table 14 shows the results and the isomerization conditions.

TABLE 1

|  | Reaction temperature | Contact time | Reaction product composition (GC %) | | | | 1234Z Post-distillation purity |
|---|---|---|---|---|---|---|---|
|  | ° C. | s | 1234E | 1234zc | 245fa | 1234Z |  |
| Material |  |  | 99.94 | — | 0.03 | 0.03 |  |
| Comparative example 1 | 200 | 1000 | 85.38 | 0.01 | 0.19 | 14.38 | 98.70 |
| Example 1 |  | 455 | 85.44 | 0.01 | 0.17 | 14.37 | 98.86 |
| Example 2 |  | 231 | 85.51 | 0.01 | 0.14 | 14.33 | 99.04 |
| Example 3 |  | 180 | 85.46 | 0.01 | 0.13 | 14.39 | 99.08 |
| Example 4 |  | 120 | 85.37 | 0.01 | 0.12 | 14.50 | 99.21 |
| Example 5 |  | 30 | 85.58 | 0.01 | 0.07 | 14.34 | 99.52 |
| Comparative example 2 | 300 | 1000 | 88.54 | 0.06 | 0.59 | 18.79 | 96.96 |
| Example 6 |  | 189 | 80.66 | 0.04 | 0.37 | 18.90 | 98.06 |
| Example 7 |  | 117 | 80.84 | 0.04 | 0.23 | 18.87 | 98.78 |
| Example 8 |  | 106 | 80.94 | 0.04 | 0.19 | 18.83 | 99.01 |
| Example 9 |  | 62 | 81.00 | 0.04 | 0.15 | 18.81 | 99.22 |
| Comparative example 3 | 400 | 1000 | 78.18 | 0.13 | 0.68 | 21.22 | 96.89 |
| Example 10 |  | 120 | 78.24 | 0.09 | 0.31 | 21.31 | 98.58 |
| Example 11 |  | 88 | 78.49 | 0.09 | 0.27 | 21.12 | 98.76 |
| Example 12 |  | 78 | 78.44 | 0.09 | 0.24 | 21.20 | 98.87 |
| Example 13 |  | 61 | 78.32 | 0.09 | 0.20 | 21.38 | 99.06 |
| Example 14 |  | 30 | 77.97 | 0.10 | 0.12 | 21.81 | 99.46 |
| Comparative example 4 | 500 | 200 | 65.39 | 0.39 | 1.54 | 19.34 | 92.62 |
| Example 15 |  | 30 | 68.13 | 0.25 | 0.23 | 21.86 | 98.96 |
| Example 16 |  | 12 | 70.79 | 0.32 | 0.09 | 23.70 | 99.62 |
| Example 17 |  | 5 | 74.75 | 0.37 | 0.03 | 24.61 | 99.87 |
| Comparative example 5 | 147 | 44 | 99.40 | — | 0.04 | 0.56 | — |

TABLE 2

|  | Reaction temperature | Contact time | Reaction product composition (GC %) | | | | 1234Z Post-distillation purity |
|---|---|---|---|---|---|---|---|
|  | ° C. | s | 1234E | 1234zc | 245fa | 1234Z |  |
| Material |  |  | 99.94 | — | 0.03 | 0.03 |  |
| Example 18 | 200 | 225 | 95.10 | 0.01 | 0.03 | 4.87 | 99.39 |
| Example 19 | 250 | 219 | 92.02 | 0.02 | 0.02 | 7.94 | 99.75 |
| Example 20 | 300 | 178 | 82.90 | 0.02 | 0.03 | 17.05 | 99.82 |
| Example 21 | 400 | 156 | 78.57 | 0.07 | 0.04 | 21.30 | 99.79 |
| Example 22 |  | 59 | 79.41 | 0.06 | 0.04 | 20.49 | 99.83 |
| Example 23 | 500 | 162 | 75.01 | 0.36 | 0.25 | 23.45 | 98.94 |
| Example 24 |  | 59 | 75.81 | 0.19 | 0.07 | 23.54 | 99.70 |
| Example 25 |  | 30 | 75.64 | 0.20 | 0.04 | 23.52 | 99.82 |

TABLE 3

|  | Reaction temperature | Contact time | Reaction product composition (GC %) | | | | 1234Z Post-distillation purity |
|---|---|---|---|---|---|---|---|
|  | ° C. | s | 1234E | 1234zc | 245fa | 1234Z |  |
| Material |  |  | 99.94 | — | 0.03 | 0.03 |  |
| Example 26 | 300 | 463 | 84.59 | 0.03 | 0.02 | 15.36 | 99.88 |
| Example 27 |  | 61 | 94.79 | 0.03 | 0.02 | 5.16 | 99.59 |
| Example 28 |  | 30 | 97.13 | 0.03 | 0.02 | 2.81 | 99.19 |
| Example 29 | 400 | 60 | 79.43 | 0.08 | 0.02 | 20.49 | 99.91 |
| Example 30 |  | 30 | 82.82 | 0.07 | 0.02 | 17.05 | 99.89 |
| Example 31 | 500 | 58 | 74.91 | 0.14 | 0.05 | 24.89 | 99.82 |
| Example 32 |  | 30 | 74.70 | 0.13 | 0.04 | 25.12 | 99.83 |

TABLE 4

| | Reaction temperature | Contact time | Reaction product composition (GC %) | | | | 1234Z Post-distillation purity |
|---|---|---|---|---|---|---|---|
| | °C. | s | 1234E | 1234zc | 245fa | 1234Z | |
| | Material | | 99.94 | — | 0.03 | 0.03 | |
| Example 33 | 300 | 87 | 95.56 | — | 0.04 | 4.40 | 99.01 |
| Example 34 | | 45 | 96.72 | — | 0.04 | 3.24 | 98.81 |
| Example 35 | 400 | 167 | 89.64 | — | 0.22 | 10.15 | 97.91 |
| Example 36 | | 94 | 90.79 | — | 0.10 | 9.10 | 98.89 |
| Example 37 | | 47 | 92.34 | — | 0.06 | 7.60 | 99.16 |
| Example 38 | | 29 | 94.03 | — | 0.04 | 5.93 | 99.28 |
| Example 39 | | 15 | 95.01 | — | 0.05 | 4.94 | 99.08 |
| Example 40 | 500 | 29 | 89.84 | — | 0.22 | 9.93 | 97.80 |
| Example 41 | | 15 | 91.06 | — | 0.12 | 8.81 | 98.61 |
| Example 42 | | 9 | 91.44 | 0.01 | 0.07 | 8.49 | 99.24 |

TABLE 5

| | Reaction temperature | Contact time | Reaction product composition (GC %) | | | | 1234Z Post-distillation purity |
|---|---|---|---|---|---|---|---|
| | °C. | s | 1234E | 1234zc | 245fa | 1234Z | |
| | Material | | 99.94 | — | 0.03 | 0.03 | |
| Example 43 | 400 | 66 | 88.65 | 0.06 | 0.03 | 11.23 | 99.72 |
| Example 44 | 500 | 132 | 84.65 | 0.10 | 0.14 | 15.00 | 99.09 |
| Example 45 | | 63 | 86.70 | 0.10 | 0.08 | 13.04 | 99.38 |
| Example 46 | | 30 | 92.67 | 0.11 | 0.04 | 7.12 | 99.48 |

TABLE 6

| | Reaction temperature | Contact time | Reaction product composition (GC %) | | | | 1234Z Post-distillation purity |
|---|---|---|---|---|---|---|---|
| | °C. | s | 1234E | 1234zc | 245fa | 1234Z | |
| | Material | | 99.88 | — | 0.06 | 0.06 | |
| Example 47 | 200 | 58.7 | 85.60 | — | 0.07 | 14.32 | 99.53 |
| Example 48 | | 30.5 | 85.58 | 0.01 | 0.05 | 14.36 | 99.64 |
| Example 49 | | 14.0 | 85.66 | 0.01 | 0.04 | 14.29 | 99.71 |
| Example 50 | | 8.5 | 85.46 | 0.01 | 0.05 | 14.48 | 99.69 |
| Example 51 | 300 | 73.9 | 80.76 | 0.02 | 1.10 | 17.85 | 94.22 |
| Example 52 | | 22.7 | 81.93 | 0.02 | 0.60 | 17.43 | 96.68 |
| Example 53 | | 12.2 | 81.99 | 0.02 | 0.39 | 17.59 | 97.81 |
| Example 54 | | 7.5 | 81.82 | 0.02 | 0.26 | 17.90 | 98.59 |
| Example 55 | 400 | 63.6 | 73.61 | 0.04 | 2.31 | 16.48 | 87.71 |
| Example 56 | | 14.3 | 79.90 | 0.04 | 0.89 | 18.27 | 95.35 |
| Example 57 | | 5.1 | 79.54 | 0.06 | 0.29 | 20.05 | 98.57 |

TABLE 7

| | Reaction temperature | Contact time | Reaction product composition (GC %) | | | | 1234Z Post-distillation purity |
|---|---|---|---|---|---|---|---|
| | °C. | s | 1234E | 1234zc | 245fa | 1234Z | |
| | Material | | 99.96 | — | 0.01 | 0.02 | |
| Example 58 | 200 | 109.6 | 87.26 | — | 0.02 | 12.72 | 99.84 |
| Example 59 | | 60.6 | 91.20 | — | 0.01 | 8.78 | 99.85 |
| Example 60 | | 14.7 | 97.91 | — | 0.02 | 2.07 | 99.05 |
| Example 61 | 300 | 156.7 | 83.54 | 0.01 | 0.81 | 15.53 | 95.02 |
| Example 62 | | 59.6 | 82.37 | 0.02 | 0.20 | 17.38 | 98.87 |

TABLE 7-continued

|  | Reaction temperature | Contact time | Reaction product composition (GC %) | | | | 1234Z Post-distillation purity |
|---|---|---|---|---|---|---|---|
|  | ° C. | s | 1234E | 1234zc | 245fa | 1234Z | |
| Example 63 |  | 18.8 | 82.39 | 0.02 | 0.06 | 17.52 | 99.65 |
| Example 64 | 400 | 132.9 | 78.24 | 0.10 | 2.06 | 18.94 | 90.18 |
| Example 65 |  | 33.8 | 79.83 | 0.05 | 0.52 | 19.33 | 97.40 |
| Example 66 |  | 13.9 | 80.10 | 0.05 | 0.15 | 19.64 | 99.25 |
| Example 67 | 500 | 61.1 | 67.82 | 0.47 | 1.48 | 18.71 | 92.68 |
| Example 68 |  | 14.9 | 79.29 | 0.09 | 0.12 | 20.29 | 99.42 |

TABLE 8

|  | Reaction temperature | Contact time | Reaction product composition (GC %) | | | | 1234Z Post-distillation purity |
|---|---|---|---|---|---|---|---|
|  | ° C. | s | 1234E | 1234zc | 245fa | 1234Z | |
|  | Material |  | 99.93 | — | 0.04 | 0.02 |  |
| Example 69 | 200 | 127 | 99.36 | — | 0.02 | 0.62 | 97.48 |
| Example 70 | 300 | 109 | 96.65 | 0.04 | 0.02 | 3.29 | 99.43 |
| Example 71 |  | 69 | 98.10 | 0.03 | 0.02 | 1.85 | 98.88 |
| Example 72 | 400 | 117 | 80.74 | 0.18 | 0.02 | 18.62 | 99.90 |
| Example 73 |  | 59 | 88.44 | 0.15 | 0.02 | 11.39 | 99.82 |
| Example 74 |  | 27 | 95.34 | 0.10 | 0.03 | 4.52 | 99.41 |
| Example 75 |  | 6 | 99.20 | 0.04 | 0.03 | 0.73 | 96.43 |
| Example 76 | 500 | 191 | 71.60 | 0.24 | 0.21 | 22.02 | 99.06 |
| Example 77 |  | 117 | 71.37 | 0.22 | 0.08 | 22.42 | 99.66 |
| Example 78 |  | 61 | 74.23 | 0.24 | 0.06 | 21.64 | 99.74 |
| Example 79 |  | 42 | 78.66 | 0.29 | 0.18 | 18.50 | 99.02 |
| Example 80 |  | 7 | 97.27 | 0.04 | 0.03 | 2.66 | 98.85 |

TABLE 9

|  | Reaction temperature | Contact time | Reaction product composition (GC %) | | | | 1234Z Post-distillation purity |
|---|---|---|---|---|---|---|---|
|  | ° C. | s | 1234E | 1234zc | 245fa | 1234Z | |
|  | Material |  | 99.95 | — | 0.02 | 0.03 |  |
| Example 81 | 200 | 117 | 97.00 | 0.01 | 0.02 | 2.98 | 99.37 |
| Example 82 |  | 64 | 98.25 | 0.01 | 0.02 | 1.72 | 98.62 |
| Example 83 | 300 | 109 | 84.55 | 0.06 | 0.03 | 15.36 | 99.83 |
| Example 84 |  | 64 | 87.82 | 0.06 | 0.03 | 12.09 | 99.77 |
| Example 85 |  | 42 | 89.94 | 0.05 | 0.03 | 10.04 | 99.66 |
| Example 86 |  | 24 | 93.07 | 0.05 | 0.03 | 6.85 | 99.56 |
| Example 87 |  | 10 | 97.27 | 0.04 | 0.03 | 2.66 | 98.85 |
| Example 88 |  | 6 | 98.70 | 0.03 | 0.03 | 1.23 | 97.31 |
| Example 89 | 400 | 109 | 73.90 | 0.23 | 0.28 | 21.46 | 98.70 |
| Example 90 |  | 61 | 74.12 | 0.23 | 0.21 | 21.34 | 99.03 |
| Example 91 |  | 26 | 75.85 | 0.21 | 0.05 | 21.25 | 99.79 |
| Example 92 |  | 10 | 85.55 | 0.18 | 0.02 | 13.59 | 99.82 |

TABLE 10

|  | Reaction temperature | Contact time | Reaction product composition (GC %) | | | | 1234Z Post-distillation purity |
|---|---|---|---|---|---|---|---|
|  | ° C. | s | 1234E | 1234zc | 245fa | 1234Z | |
|  | Material |  | 99.96 | — | 0.0148 | 0.02 |  |
| Example 93 | 200 | 55.9 | 90.90 | — | 0.05 | 9.03 | 99.46 |

TABLE 10-continued

|  | Reaction temperature | Contact time | Reaction product composition (GC %) | | | | 1234Z Post-distillation purity |
|---|---|---|---|---|---|---|---|
|  | ° C. | s | 1234E | 1234zc | 245fa | 1234Z |  |
| Example 94 |  | 21.7 | 95.64 | — | 0.05 | 4.30 | 98.90 |
| Example 95 |  | 13.1 | 96.93 | — | 0.08 | 2.98 | 97.42 |
| Example 96 | 300 | 56.5 | 82.38 | 0.02 | 0.61 | 16.67 | 96.46 |
| Example 97 |  | 21.9 | 85.87 | 0.02 | 0.09 | 13.31 | 99.30 |
| Example 98 |  | 8.7 | 91.01 | 0.02 | 0.04 | 8.86 | 99.58 |

TABLE 11

|  | Reaction temperature | Contact time | Reaction product composition (GC %) | | | | 1234Z Post-distillation purity |
|---|---|---|---|---|---|---|---|
|  | ° C. | s | 1234E | 1234zc | 245fa | 1234Z |  |
|  | Material |  | 99.96 | — | 0.02 | 0.02 |  |
| Example 99 | 200 | 163.8 | 91.49 | 0.00 | 0.02 | 8.43 | 99.77 |
| Example 100 |  | 64.9 | 95.14 | 0.00 | 0.02 | 4.80 | 99.61 |
| Example 101 |  | 30.6 | 96.63 | 0.00 | 0.02 | 3.34 | 99.41 |
| Example 102 | 300 | 161.5 | 79.77 | 0.04 | 0.59 | 18.35 | 96.90 |
| Example 103 |  | 66.4 | 80.00 | 0.04 | 0.20 | 18.58 | 98.92 |
| Example 104 |  | 30.7 | 80.94 | 0.04 | 0.08 | 18.72 | 99.58 |
| Example 105 | 400 | 66.4 | 72.69 | 0.10 | 1.17 | 20.61 | 94.63 |
| Example 106 |  | 30.8 | 77.56 | 0.11 | 0.10 | 21.87 | 99.55 |
| Example 107 |  | 20.6 | 77.61 | 0.12 | 0.04 | 22.12 | 99.81 |
| Example 108 | 500 | 157.3 | 75.06 | 0.23 | 0.14 | 23.31 | 99.40 |
| Example 109 |  | 66.1 | 75.49 | 0.22 | 0.06 | 23.70 | 99.74 |
| Example 110 |  | 31.3 | 75.28 | 0.25 | 0.06 | 23.89 | 99.74 |
| Example 111 |  | 9.9 | 81.23 | 0.26 | 0.03 | 18.41 | 99.83 |

TABLE 12

|  | Reaction temperature | Contact time | Reaction product composition (GC %) | | | | 1234Z Post-distillation purity |
|---|---|---|---|---|---|---|---|
|  | ° C. | s | 1234E | 1234zc | 245fa | 1234Z |  |
|  | Material |  | 99.94 | — | 0.03 | 0.03 |  |
| Example 112 | 150 | 119 | 89.13 | — | 0.05 | 10.81 | 99.59 |
| Example 113 |  | 60 | 90.75 | — | 0.04 | 9.21 | 99.61 |
| Example 114 |  | 29 | 92.75 | — | 0.04 | 7.21 | 99.46 |
| Example 115 | 200 | 55 | 85.03 | 0.01 | 0.30 | 14.83 | 97.97 |
| Example 116 |  | 31 | 85.89 | 0.01 | 0.08 | 13.93 | 99.42 |
| Example 117 |  | 16 | 87.74 | 0.01 | 0.05 | 12.16 | 99.59 |

TABLE 13

|  | Reaction temperature | Contact time | Reaction product composition (GC %) | | | | 1234Z Post-distillation purity |
|---|---|---|---|---|---|---|---|
|  | ° C. | s | 1234E | 1234zc | 245fa | 1234Z |  |
|  | Material |  | 99.94 | — | 0.03 | 0.03 |  |
| Example 118 | 100 | 112 | 90.28 | — | 0.13 | 9.57 | 98.64 |
| Example 119 |  | 63 | 90.54 | — | 0.08 | 9.37 | 99.15 |
| Example 120 |  | 31 | 90.95 | — | 0.10 | 8.95 | 98.95 |
| Example 121 | 200 | 60 | 93.12 | 0.01 | 0.33 | 15.98 | 97.96 |
| Example 122 |  | 31 | 83.50 | 0.01 | 0.14 | 16.10 | 99.17 |
| Example 123 |  | 17 | 83.54 | 0.01 | 0.10 | 16.17 | 99.37 |
| Example 124 | 250 | 60 | 80.87 | 0.02 | 0.32 | 18.49 | 98.31 |

TABLE 13-continued

| | Reaction temperature | Contact time | Reaction product composition (GC %) | | | | 1234Z Post-distillation purity |
|---|---|---|---|---|---|---|---|
| | °C. | s | 1234E | 1234zc | 245fa | 1234Z | |
| Example 125 | | 32 | 81.12 | 0.03 | 0.27 | 18.18 | 98.54 |
| Example 126 | | 16 | 80.95 | 0.02 | 0.09 | 18.74 | 99.55 |

TABLE 14

| | Reaction temperature | Contact time | Reaction product composition (GC %) | | | | 1234Z Post-distillation purity |
|---|---|---|---|---|---|---|---|
| | °C. | s | 1234E | 1234zc | 245fa | 1234Z | |
| Material | | | 99.94 | — | 0.03 | | |
| Example 127 | 300 | 117 | 97.78 | 0.02 | 0.02 | 2.18 | 98.91 |
| Example 128 | 400 | 117 | 93.39 | 0.05 | 0.02 | 6.54 | 99.71 |
| Example 129 | | 53 | 96.71 | 0.06 | 0.03 | 3.19 | 98.95 |
| Example 130 | 500 | 153 | 80.82 | 0.13 | 0.03 | 18.50 | 99.82 |
| Example 131 | | 80 | 84.45 | 0.13 | 0.03 | 15.21 | 99.81 |
| Example 132 | | 24 | 93.84 | 0.15 | 0.04 | 5.92 | 99.31 |
| Example 133 | | 6 | 97.50 | 0.17 | 0.04 | 2.29 | 98.33 |

Referring to Table 1, the results in examples 1 to 5, examples 6 to 9, and examples 10 to 14 in which the isomerization conditions were within the ranges according to the present invention were respectively compared with the results in comparative examples 1, 2 and 3 in which the isomerization conditions were outside the ranges according to the present invention except that the reaction temperatures were respectively the same as those in examples 1 to 5, examples 6 to 9, and examples 10 to 14. In comparative examples 1 to 3, 1,1,1,3,3-pentafluoropropane (245fa) was produced as a byproduct in a large amount by the isomerization reaction, and thus highly pure cis-1,3,3,3-tetrafluoropropene (1234Z) was not obtained even when the resultant product was distilled. By contrast, in examples 1 to 17 in which the conditions were within the ranges according to the present invention, highly pure cis-1,3,3,3-tetrafluoropropene (1234Z) having a purity of approximately 99.9% by mass was obtained by distillation. In comparative example 4, the isomerization reaction was performed at a reaction temperature of 500° C. and with a contact time of 200 seconds. As compared with examples 15 to 17 in which the same reaction temperature was applied but the contact time was shorter than or equal to 30 seconds, 1,1,1,3,3-pentafluoropropane (245fa) was produced as a byproduct in a larger amount in comparative example 4. From this, it is found that an appropriate combination of reaction temperature and contact time is an important element for the isomerization reaction according to the present invention. In comparative example 5, the reaction was performed at a low reaction temperature of 147° C. The isomerization reaction did not advance in comparative example 5. Referring to Tables 2 to 14, in most of examples 18 to 133 in which the isomerization reaction was performed under the conditions in the ranges according to the present invention, highly pure cis-1,3,3,3-tetrafluoropropene (1234Z) was obtained.

The method according to the present invention produces highly pure 1234Z efficiently, and therefore is suitable for industrial production of polyurethane foaming agents, fluxes, washing detergents, coolants, working fluids, sprays, agromedical intermediates, materials of fluorine resins and the like.

The invention claimed is:

1. A method for producing cis-1,3,3,3-tetrafluoropropene comprising;
    contacting trans-1,3,3,3-tetrafluoropropene with a catalyst at a reaction temperature of higher than or equal to 200° C. and lower than or equal to 550° C. for a contact time of longer than or equal to 0.01 seconds and shorter than or equal to 500 seconds,
    wherein the reaction temperature and the contact time have negative correlation and wherein the product obtained by contacting trans-1,3,3,3-tetrafluoropropene with the catalyst is substantially free of 1,1,1,3,3-pentafluoropropane.

2. The method according to claim 1, wherein the reaction temperature is higher than or equal to 250° C. and lower than or equal to 500° C. and the contact time is longer than or equal to 1 second and shorter than or equal to 150 seconds.

3. The method according to claim 1, wherein contacting the trans-1,3,3,3-tetrafluoropropene with the catalyst comprises contacting the trans-1,3,3,3-tetrafluoropropene with a gas phase.

4. The method according to claim 1, wherein the catalyst is a metal compound comprising at least one metal material selected from the group consisting of aluminum, chromium, titanium, manganese, iron, nickel, cobalt, copper, magnesium, zirconium, molybdenum, zinc, tin, lanthanum and antimony.

5. The method according to claim 4, wherein the metal compound is a metal fluoride.

6. A method for producing highly pure cis-1,3,3,3-tetrafluoropropene, comprising;
    distilling cis-1,3,3,3-tetrafluoropropene obtained by a method according to claim 1.

7. A method for producing cis-1,3,3,3-tetrafluoropropene including;

putting trans-1,3,3,3-tetrafluoropropene into contact with a catalyst at a reaction temperature of higher than or equal to 200° C. and lower than or equal to 550° C. for a contact time of longer than or equal to 0.01 seconds and shorter than or equal to 500 seconds, wherein the catalyst is a supported catalyst in which a metal compound comprising at least one metal material selected from the group consisting of aluminum, chromium, titanium, manganese, iron, nickel, cobalt, copper, magnesium, zirconium, molybdenum, zinc, tin, lanthanum and antimony is supported on carbon, and the reaction temperature and the contact time have negative correlation and wherein the product obtained by contacting trans-1,3,3,3-tetrafluoropropene with the catalyst is substantially free of 1,1,1,3,3-pentafluoropropane.

8. The method according to claim 1, wherein the catalyst is the metal compound comprising at least one metal material selected from a group consisting of aluminum, titanium, manganese, iron, nickel, cobalt, copper, magnesium, zirconium, molybdenum, zinc, tin, lanthanum and antimony.

9. The method according to claim 1, wherein a product obtained by contacting trans-1,3,3,3-tetrafluoropropene with the catalyst is substantially free of other materials except for cis-1,3,3,3-tetrafluoropropene and trans-1,3,3,3-tetrafluoropropene.

10. The method according to claim 7, wherein the catalyst is the supported catalyst in which the metal compound comprising at least one metal material selected from the group consisting of aluminum, titanium, manganese, iron, nickel, cobalt, copper, magnesium, zirconium, molybdenum, zinc, tin, lanthanum and antimony is supported on carbon.

11. The method according to claim 7, wherein a product obtained by putting trans-1,3,3,3-tetrafluoropropene into contact with the catalyst is substantially free of other materials except for cis-1,3,3,3-tetrafluoropropene and trans-1,3,3,3-tetrafluoropropene.

* * * * *